United States Patent [19]

Tanaka et al.

[11] Patent Number: 5,237,092

[45] Date of Patent: Aug. 17, 1993

[54] PROCESS FOR CONCURRENTLY PRODUCING ARYL FORMATE AND AROMATIC CARBOXYLIC ACID

[75] Inventors: Toru Tanaka; Kazuo Tanaka; Teruo Aratake, all of Kurashiki, Japan

[73] Assignee: Mitsubishi Gas Chemical Company, Inc., Tokyo, Japan

[21] Appl. No.: 899,313

[22] Filed: Jun. 16, 1992

[30] Foreign Application Priority Data

Jun. 26, 1991 [JP] Japan ................... 3-181982

[51] Int. Cl.⁵ .................... C07C 67/39; C07C 51/235
[52] U.S. Cl. ............................ 560/238; 560/64; 560/71; 560/101; 560/103; 560/254; 562/5; 562/421; 562/469; 562/473; 562/490; 562/492; 562/493
[58] Field of Search ............... 560/238, 254; 562/421, 562/493, 469, 473, 490, 492, 5

[56] References Cited

U.S. PATENT DOCUMENTS

| | | | |
|---|---|---|---|
| 3,579,575 | 5/1971 | Bouniot | 560/238 X |
| 3,709,923 | 1/1973 | Stapp | 560/238 X |
| 3,816,522 | 1/1974 | Goldstein | 560/238 X |
| 3,919,305 | 11/1975 | Gay | 560/238 X |

FOREIGN PATENT DOCUMENTS

| | | |
|---|---|---|
| 2263216 | 10/1975 | France . |
| 2297832 | 8/1976 | France . |
| 992017 | 5/1965 | United Kingdom . |

OTHER PUBLICATIONS

Chem. Abstr., vol. III, p. 690, (1989), Abstract No. 173776w, Abstracting JP-A-01117859.
Chem. Abstr., vol. 94, p. 534, (1981), Abstract No. 30376j Abstracting JP-A-55027904.
Chem. Abstr., vol. 88, p. 507 (1978), Abstract No. 136319k Abstracting JP-A-52148037.

Primary Examiner—José G. Dees
Assistant Examiner—Vera C. Clarke
Attorney, Agent, or Firm—Wenderoth, Lind & Ponack

[57] ABSTRACT

A process for efficiently producing aryl formate and aromatic carboxylic acid from aldehyde, which comprises oxidizing an aromatic aldehyde with an oxygen-containing gas in the presence of a volatile solvent up to a reaction ratio of 40 to 70 mol % to convert the aromatic aldehyde to a peracid, adding a stabilizer, and allowing the remaining aromatic aldehyde and the aromatic peracid to react while the volatile solvent is distilled off.

9 Claims, No Drawings

5,237,092

PROCESS FOR CONCURRENTLY PRODUCING ARYL FORMATE AND AROMATIC CARBOXYLIC ACID

FIELD OF THE INVENTION

The present invention relates to a process for producing aryl formate and aromatic carboxylic acid from aromatic aldehyde. Aryl formate is a precursor for the production of alkyl phenol useful as an antioxidant, and aromatic carboxylic acid is useful as a stabilizer for vinyl chloride.

PRIOR ART OF THE INVENTION

It is known that an ester is formed by reacting ketone with peracid, and this process is referred to as Baeyer-Villinger rearrangement. In this reaction, hydrogen peroxide can be also used. Japanese Patent Publication No. 10243/1969 discloses a process for producing an ester in which Baeyer-Villinger rearrangement is carried out by the use of hydrogen peroxide in the presence of an arsenic compound. As a process for producing peracid, U.K. Patent 992,017 discloses a process for producing peracetic acid in which acetaldehyde is oxidized, and Japanese Patent Publications Nos. 27904/1980 and 46392/1980 disclose a process for producing per-p-toluic acid in which p-tolualdehyde is oxidized.

Aryl formate can be obtained by allowing aromatic aldehyde and peracid to react according to Baeyer-Villinger rearrangement. However, peracid and hydrogen peroxide are relatively expensive, and handling of these is dangerous. Aromatic peracid is less dangerous than any one of hydrogen peroxide, performic acid and peracetic acid. Therefore, it is conceivable to employ a method in which aromatic aldehyde is converted to aromatic peracid, and aromatic aldehyde and the aromatic peracid are subjected to Baeyer-Villinger rearrangement to produce aryl formate and aromatic carboxylic acid.

Since, however, the above method involves the following problems, it is difficult to effectively produce aryl formate and aromatic carboxylic acid.

(1) Unreacted aromatic aldehyde and the corresponding aryl formate are little different in boiling point, and it is hence difficult to separate these two compounds from each other by distillation. It is therefore desirable to decrease the amount of unreacted aromatic aldehyde as much as possible. When the amount of the unreacted aromatic aldehyde is decreased, the reflux amount in the separation of the aryl formate from the aromatic aldehyde can be greatly reduced, and the volume of heat required for the separation can be therefore greatly reduced.

(2) For the purpose of decreasing unreacted aromatic aldehyde, it is conceivable to employ a method in which aromatic aldehyde is oxidized as a whole to form aromatic peracid, and the aromatic peracid is allowed to react with aromatic aldehyde to produce aryl formate and aromatic carboxylic acid. In this method, the amount of unreacted aromatic aldehyde is small. However, the selectivity to aromatic carboxylic acid is high, and the selectivity to aryl formate is extraordinarily low.

(3) In making an attempt to obtain aromatic peracid by oxidation of aromatic aldehyde in the absence of a solvent, if the control of the reaction rate is not enough, aromatic peracid and aromatic carboxylic acid are formed in large quantities since aromatic peracid and aromatic carboxylic acid are crystallizable, which formation in large quantities may cause a dangerous state. Further, there may be formed a byproduct which is to terminate the reaction. When the reaction for the above formation is carried out in the presence of a solvent, the precipitation of the crystals may be inhibited. It may be possible to carry out the oxidation in a uniform solution state, and the reaction may be moderately continued since the reactants are diluted. However, the reaction between aromatic aldehyde and aromatic peracid in the presence of a solvent shows a low reaction rate and requires a large-scale reactor.

SUMMARY OF THE INVENTION

It is an object of the present invention to provide a process for effectively producing aryl formate and aromatic carboxylic acid from aromatic aldehyde.

It is another object of the present invention to provide a process for producing aryl formate and aromatic carboxylic acid from aromatic aldehyde, which process enables the reduction of unreacted aromatic aldehyde in a reaction liquid and the improvement of the selectivity to aryl formate.

It is further object of the present invention to provide a process for producing aryl formate and aromatic carboxylic acid from aromatic aldehyde, which process enables the reduction of the formation of aromatic carboxylic acid other than aromatic peracid and the reduction of the amount of unreacted aromatic aldehyde by controlling the reaction rate of aromatic aldehyde to aromatic peracid in a proper range.

It is a still further object of the present invention to provide a process for producing aryl formate and aromatic carboxylic acid from aromatic aldehyde, which process enables the economical separation of aromatic aldehyde and aryl formate from each other by distillation by decreasing unreacted aromatic aldehyde.

Further, it is an object of the present invention to provide a process for producing aryl formate and aromatic carboxylic acid from aromatic aldehyde in the presence of a solvent, in which the reaction rate between aromatic aldehyde and aromatic peracid is high in spite of the presence of the solvent.

According to the present invention, there is provided a process for producing an aryl formate and an aromatic carboxylic acid, which comprises oxidizing an aromatic aldehyde with an oxygen-containing gas in the presence of a volatile solvent up to a reaction ratio of 40 to 70 mol % to convert the aromatic aldehyde to a peracid, adding a stabilizer, and allowing the remaining aromatic aldehyde and the aromatic peracid to react while the volatile solvent is distilled off.

DETAILED DESCRIPTION OF THE INVENTION

The present inventors have made a diligent study on a process for producing aryl formate and aromatic carboxylic acid, which process involves the above-described problems, and found that aryl formate and aromatic carboxylic acid can be concurrently and efficiently produced by oxidizing aromatic aldehyde in the presence of a volatile solvent up to a predetermined reaction ratio to form a solution containing the resultant aromatic peracid and the remaining aromatic aldehyde, then adding a stabilizer, and allowing the aromatic aldehyde and the aromatic peracid to react while the volatile solvent is distilled off.

The aromatic aldehyde used in the present invention includes benzaldehyde, tolualdehyde, dimethylbenzaldehyde, trimethylbenzaldehyde, ethylbenzaldehyde, methoxybenzaldehyde, cuminaldehyde, biphenylaldehyde, butylbenzaldehyde, phenoxyaldehyde, hydroxybenzaldehyde and cyclohexylbenzaldehyde. In particular, tolualdehyde, dimethylbenzaldehyde and trimethylbenzaldehyde are preferably used in the present invention since these are industrially mass-produced.

In the first step of the present invention for the synthesis of an aromatic peracid, a volatile solvent is used. This volatile solvent is required to be inert to the oxidation reaction. The volatile solvent includes ketones such as acetone and methyl ethyl ketone, and esters such as ethyl acetate and ethyl benzoate. Particularly preferred are acetone and ethyl acetate. The concentration of aromatic aldehyde in the solution containing the aromatic aldehyde and the solvent is approximately 10 to 40% by weight.

The synthesis of the aromatic peracid can be carried out in the absence of a catalyst. However, it is preferred to use a metal catalyst such as cobalt, manganese, iron, platinum, palladium, vanadium, ruthenium, zirconium, aluminum, antimony, beryllium and copper. A cobalt catalyst is particularly preferred. For example, when a cobalt catalyst is used, the amount of the cobalt catalyst based on the total amount of a reaction solution is 0.1 to 50 ppm, preferably 0.5 to 10 ppm. When this amount is less than 0.1 ppm, the reaction rate is low. When this amount exceeds 50 ppm, the selectivity to aromatic peracid decreases.

The aromatic peracid is synthesized by oxidizing the aromatic aldehyde with an oxygen-containing gas. The oxygen-containing gas is introduced in the form of pure oxygen, air, air having an increased oxygen concentration, or a mixed gas containing oxygen and an inert gas (carbon dioxide, nitrogen, etc.). Air is generally used.

The reaction temperature for the synthesis of the aromatic peracid differs depending upon the kind of the aromatic aldehyde used as a starting material and the catalyst. However, the reaction temperature is generally in the range of $-20°$ to $150°$ C., preferably in the range of $30°$ to $80°$ C. When the reaction temperature is too low, the reaction rate is low. When the reaction temperature is too high, the selectivity to the aromatic peracid is low.

The reaction pressure for the synthesis of the aromatic peracid is generally in the range of atmospheric pressure to $60$ $kg/cm^2G$, preferably in the range of 4 to 50 $kg/cm^2G$. With an increase in the reaction pressure, the reaction rate tends to increase, and the yield of the aromatic peracid tends to increase. Further, the dissipation of the solvent out of the reaction system can be prevented. It is therefore preferred to carry out the peracid synthesis under an elevated pressure. However, even if the reaction pressure exceeds $60$ $kg/cm^2G$, no further effect is obtained.

In the present invention, the reaction ratio of the aromatic aldehyde in the aromatic peracid synthesis is set at 40 to 70 mol %. The aromatic peracid synthesis might be carried out by a method in which the aromatic aldehyde is oxidized up to about 100 mol % and the resultant aromatic peracid and newly added aromatic aldehyde are subjected to a Baeyer-Villinger reaction. However, when the reaction ratio of the aromatic aldehyde is increased up to more than 70 mol %, the formation of an aromatic carboxylic acid other than the aromatic peracid increases, and as a result, the selectivity to the aryl formate to be produced from the aromatic aldehyde decreases. When the reaction ratio of the aromatic aldehyde is set at lower than 40 mol %, the selectivity to the aryl formate based on the aromatic aldehyde increases, whereas the amount of unreacted aromatic aldehyde is large. An aromatic aldehyde and the corresponding aryl formate generally have little difference in boiling point. It is therefore difficult to separate the aromatic aldehyde and the aryl formate by distillation.

In the present invention, the reaction ratio of the aromatic aldehyde for the formation of aromatic peracid synthesis is set in the range of 40 to 70 mol %. As a result, the selectivity to the aryl formate to be produced from the aromatic aldehyde is high, and the reaction to form the aryl formate from the aromatic aldehyde is effectively carried out. Moreover, the present invention solves the above problem on the separation of the aromatic aldehyde and the aryl formate by distillation.

Immediately after the aromatic peracid is synthesized, a stabilizer is added to stabilize the so-obtained peracid. The stabilizer includes sodium pyrophosphate, 8-oxyquinoline, dipicolinic acid, ethylene-diamine-tetracetic acid disodium salt (EDTA-2 Na) and isonicotinic acid. Dipicolinic acid is particularly preferred. The amount of the stabilizer for use is 1 to 1,000 ppm based on the aromatic peracid synthesis solution.

The so-obtained aromatic peracid synthesis solution contains unreacted aromatic aldehyde, the synthesized aromatic peracid and the volatile solvent. A Baeyer-Villinger reaction between the aromatic aldehyde and the aromatic peracid is carried out while the volatile solvent is distilled off, whereby the aryl formate and the aromatic carboxylic acid are formed. Although differing depending upon the aromatic aldehyde used as a starting material and the volatile solvent, the reaction temperature is generally in the range of $-20°$ to $150°$ C., preferably in the range of $20°$ to $100°$ C.

The pressure for the reaction between the aromatic aldehyde and the peracid is not specially limited as far as the volatile solvent can be distilled off. In general, the reaction pressure is in the range of 200 mmHg to 1,200 mmHg as absolute pressure.

It produces an effect of increasing the reaction rate and the selectivity to the aryl formate that the reaction between the aromatic aldehyde and the peracid is carried out with distilling off the volatile solvent. The reaction atmosphere may be an atmosphere of any one of nitrogen, oxygen and air. When the solution of the aromatic aldehyde and the aromatic peracid is stirred during the reaction, the aromatic peracid is liable to be decomposed and the selectivity to the aryl formate may decrease. It is therefore preferred to carry out the reaction between the aromatic aldehyde and the aromatic peracid without any stirring. After the volatile solvent is distilled off, the reaction solution is separated to an aromatic carboxylic acid and the aryl formate by distillation. The process of the present invention may be carried out by any one of a batch method and a continuous method.

The process of the present invention has features that (1) aryl formate and aromatic carboxylic acid can be produced with high selectivity by setting the reaction ratio of aromatic aldehyde for the synthesis of aromatic peracid in the above-specified range, and that (2) a high reactor space time yield can be obtained by carrying out the reaction between aromatic aldehyde and aromatic peracid with distilling off the solvent. Further, (3) aromatic peracid is relatively stable and can be industrially safely produced, and (4) aromatic aldehyde can be utilized highly efficiently. Therefore, the process of the present invention is industrially significant.

The present invention will be described more specifically hereinafter by reference to Examples. However, the present invention shall not be limited by these Examples. In Examples, "%" stands for "mol %", and "ppm" stands for "weight/weight" unless otherwise specified. The reaction ratio and the selectivity show values calculated on the following equations.

Reaction ratio=[Amount of aldehyde which reacted (mol)]/[amount of fed aldehyde (mol)]×100.

Selectivity=[Formation amount (mol)]/[Amount of aldehyde which reacted (mol)]×100.

EXAMPLE 1

An SUS316 high-pressure reactor having an internal volume of 600 ml and equipped with a stirrer and a reflux condenser was charged with 0.97 mg of $CoBr_2$ (hexahydrate) and 250 g of acetone, and while the resultant mixture was maintained under an $N_2$ pressure of 25 kg/cm$^2$G at a temperature of 35° C., 2,4-dimethylbenzaldehyde was introduced at a rate of 90 g/hour (0.672 mol/hour). Thereafter, air was also introduced, and while the oxygen concentration contained in a discharge gas was maintained at 10%, the introduction of 2,4-dimethylbenzaldehyde was continued for 45 minutes. After the introduction of 2,4-dimethylbenzaldehyde was terminated, the pressure was reduced, and 10 g of an acetone solution containing 3,900 ppm of dipicolinic acid was added.

The resultant peracid synthesis solution was composition-analyzed to show that the reaction ratio of the aldehyde was 51%, the selectivity to dimethyl perbenzoic acid was 92%, the selectivity to dimethyl benzoic acid was 4%, and the selectivity to xylenol formate was 3%.

The reactor containing the so-obtained peracid synthesis solution was immersed in a water bath kept at 70° C., and the reaction between the aldehyde and the peracid was continued for 2 hours while the acetone was distilled off at atmospheric pressure without stirring. The acetone was continuously distilled off until the solution temperature became about 70° C. The resultant reaction solution was composition-analyzed to show that the reaction ratio of the aldehyde was 88%, the selectivity to dimethyl perbenzoic acid was 1%, the selectivity to dimethyl benzoic acid was 56% and the selectivity to xylenol formate was 42%.

EXAMPLES 2 AND 3

Example 1 was repeated except that the 2,4-dimethylbenzaldehyde was replaced with p-tolualdehyde and trimethylbenzaldehyde. Table 1 shows the reaction ratios of aldehydes and the selectivities to products after the peracid synthesis and the reaction of the aldehydes with the peracids.

TABLE 1

| Aldehyde species | Example 2 p-tolu- aldehyde | Example 3 2,4,5-trimethyl benzaldehyde |
|---|---|---|
| Peracid synthesis | | |
| Reaction ratio of aldehyde | 51% | 53% |
| Selectivity to aromatic peracid | 95 | 90 |
| Selectivity to aromatic carboxylic acid | 3 | 5 |
| Selectivity to aromatic aryl formate | 1 | 4 |
| Reaction between aldehyde and peracid | | |
| Reaction ratio of aldehyde | 89% | 90% |
| Selectivity to aromatic peracid | 1 | 1 |
| Selectivity to aromatic carboxylic acid | 68 | 55 |
| Selectivity to aromatic aryl formate | 30 | 43 |

EXAMPLE 4

Example 1 was repeated except that the acetone was replaced with ethyl acetate. The reaction results after the peracid synthesis were as follows. The reaction ratio of the aldehyde was 48%, the selectivity to dimethyl perbenzoic acid was 88%, the selectivity to dimethyl benzoic acid was 7% and the selectivity to xylenol formate was 4%.

The reaction results after the reaction between the aldehyde and the peracid were as follows. The reaction ratio of the aldehyde was 85%, the selectivity to dimethyl perbenzoic acid was 2%, the selectivity to dimethyl benzoic acid was 55% and the selectivity to xylenol formate was 41%.

Comparative Example 1

Example 1 was repeated except that the introduction of air was further continued for 1.25 hours after the introduction of the aldehyde was terminated to increase the reaction ratio of the aldehyde during the synthesis of the aromatic peracid. The resultant peracid synthesis solution was composition-analyzed to show that the reaction ratio of the aldehyde was 89%, the selectivity to dimethyl perbenzoic acid was 65%, the selectivity to dimethyl benzoic acid was 28% and the selectivity to xylenol formate was 6%. The selectivity to dimethyl perbenzoic acid was greatly low as compared with the counterpart in Example 1.

EXAMPLE 5

Aromatic peracid was synthesized in the same manner as in Example 1 under the same conditions as those in Example 1. Then, the reaction between the aldehyde and the aromatic peracid was carried out in the same manner as in Example 1 except that the reaction temperature was changed to 50° C. and that the acetone was distilled off under a reduced pressure of 410 mmHg as absolute pressure. The reaction solution was composition-analyzed to show that the reaction ratio of the aldehyde was 86%, the selectivity to dimethyl perbenzoic acid was 2%, the selectivity to dimethyl benzoic acid was 57% and the selectivity to xylenol formate was 40%.

Comparative Example 2

Example 5 was repeated except that the acetone was not distilled off. The resultant reaction solution was composition-analyzed to show that the reaction ratio of the aldehyde was 70%, the selectivity to dimethyl perbenzoic acid was 29%, the selectivity to dimethyl benzoic acid was 43% and the selectivity to xylenol formate was 27%. The comparison of these data with those obtained in Example 5 showed the following. The reaction ratio of the aldehyde and the selectivity to xylenol formate were lower in this Comparative Example than in Example 5. The reason for these low reaction ratio and low selectivity is that the acetone was not distilled off.

What is claimed is:

1. A process for producing an aryl formate and an aromatic carboxylic acid, which comprises oxidizing, at a reaction temperature in the range of −20° to 150° C. and under a pressure in the range of atmospheric pressure to 60 kg/cm$^2$G, an aromatic aldehyde with an oxygen-containing gas in the presence of a ketone or an ester volatile solvent which is inert to an oxidation reaction of the aromatic aldehyde up to a reaction ratio of 40 to 70 mol % to convert the aromatic aldehyde to a peracid, adding a stabilizer, and allowing the remaining aromatic aldehyde and the aromatic peracid to react while the volatile solvent is distilled off.

2. A process according to claim 1, wherein the aromatic aldehyde is at least one member selected from the group consisting of tolualdehyde, dimethylbenzaldehyde, trimethylbenzaldehyde, ethylbenzaldehyde, methoxybenzaldehyde, cuminaldehyde, biphenylaldehyde, butylbenzaldehyde, hydroxybenzaldehyde and cyclohexylbenzaldehyde.

3. A process according to claim 1, wherein the aromatic aldehyde is oxidized in the presence of at least one metal catalyst selected the group consisting of cobalt, manganese, iron, platinum, palladium, vanadium, ruthenium, zirconium, aluminum, antimony, beryllium and copper.

4. A process according to claim 3, wherein the metal catalyst is a cobalt catalyst.

5. A process according to claim 4, wherein the cobalt catalyst is used in an amount of 0.1 to 50 ppm based on an oxidation reaction solution of the aromatic aldehyde.

6. A process according to claim 1, wherein the volatile solvent is acetone or ethyl acetate.

7. A process according to claim 1, wherein the stabilizer is at least one selected from the group consisting of sodium pyrophosphate, 8-oxyquinoline, dipicolinic acid, EDTA-2Na and isonicotinic acid.

8. A process according to claim 1, wherein the remaining aromatic aldehyde and the aromatic peracid are allowed to react at a temperature in the range of −20° to 150° C. at a pressure in the range of 200 to 1,200 mmHg.

9. A process according to claim 1, wherein the aromatic aldehyde is oxidized at a reaction temperature in the range of 30°–80° C. under a pressure in the range of 4–50 kg/cm$^2$G.

* * * * *